United States Patent [19]

Robins et al.

[11] Patent Number: 4,544,741

[45] Date of Patent: Oct. 1, 1985

[54] AZOLE DINUCLEOTIDE COMPOUNDS AND METHODS FOR THEIR PRODUCTION

[76] Inventors: Roland K. Robins, 4006 Sherwood, Provo, Utah 84604; Ganapathi R. Revankar, 1003 N. 560 East St., Orem, Utah 84057

[21] Appl. No.: 363,315

[22] Filed: Mar. 29, 1982

[51] Int. Cl.[4] ............................................. C07H 19/20
[52] U.S. Cl. ........................................................ 536/27
[58] Field of Search ........................................... 536/27

[56] References Cited

U.S. PATENT DOCUMENTS 2,951,838  9/1980  Goldman et al. ................... 536/27
4,446,315  5/1984  Marquez et al. ................... 536/27

FOREIGN PATENT DOCUMENTS 0090405  10/1983  European Pat. Off. .............. 536/27
4007517   4/1940  Japan ................................... 536/27
4012915   6/1965  Japan ................................... 536/27

OTHER PUBLICATIONS

Schiet, K., "Nucleotide Analogs", John Wiley & Sons.
Streeter et al., Biochem. & Biophys. Research Commun. 115, No. 2, pp. 544–550 (Sep. 1983).
Jayaram et al., Biochem. Pharmacology, 32 (17), 1983, pp. 2633–2636.

*Primary Examiner*—Ethel G. Love
*Attorney, Agent, or Firm*—Krass and Young

[57] ABSTRACT

A class of novel azole dinucleotide compounds and methods for their production are provided. Compounds of the class typically have pharmacological properties and are well tolerated, being useful, for example, in treating leukemias in warm blooded animals.

7 Claims, No Drawings

AZOLE DINUCLEOTIDE COMPOUNDS AND METHODS FOR THEIR PRODUCTION

TECHNICAL FIELD

This invention is directed to novel azole carboxamide dinucleotide compounds of adenosine diphosphoribose having pharmacological activity, especially antiviral and antitumor activity, and to methods for their production.

BACKGROUND OF THE INVENTION

ADP-Ribosylation can be defined as the post synthetic modification of protein by the covalent attachment of the ADP-ribose moiety of nicotinamide-adenosine dinucleotide, abbreviated NAD+. The ADP-ribosylation of nuclear proteins has recently been reviewed by M. R. Purnell, P. R. Stone, and W. J. D. Whish (*Biochem. Soc. Trans.*, 8, 215, 1980).

The enzyme responsible for ADP-ribosylation is poly (ADP-ribose) synthetase. The ADP-ribose moiety of NAD+ is cleaved at the nicotinamide-ribose bond and transferred to a protein or a protein-bound ADP-ribose molecule to give a protein bound monomer of ADP-ribose or a polymer of ADP-ribose bound covalently to specific protein. This polymer may be enzymatically degraded by an enzyme poly (ADP-ribose) glycohydrolase, which hydrolyzes the pyrophosphate bonds.

In 1958 it was suggested by R. K. Morton (*Nature*, 181 540, 1958) that NAD+ played a key role in the regulation of cellular proliferation. Hasagawa and coworkers (S. Hasagawa, S. Fujimura, Y. Shimizu and T. Sugimura: *Biochem. Biophys. Acta.*, 149, 369, 1967) pointed out that poly (ADP-ribose) synthetase modified nuclear proteins. In 1976 Rechsteiner and coworkers (M. Rechsteiner, D. Hillyard, and B. M. Olivera: *Nature*, 259, 695, 1976) showed that the cellular half-life of NAD+ is one hour, which suggests a high turnover of NAD+ due to the utilization by poly (ADP-ribose) synthetase. Thus, more adenine leaves NAD than enters DNA. Caplan and Rosenberg (A. I. Caplan and M. J. Rosenberg: *Proc. Nat'l. Acad. Sci.*, USA, 72, 1852, 1975) were the first to suggest an involvement of ADP-ribosylation in cellular differentiation which has since been supported by other workers (M. R. Purnell, P. R. Stone, and W. J. D. CWhish: *Biochem. Soc. Trans.*, 8, 215, 1980). Berger and coworkers (N. A. Berger, J. W. Adams, G. W. Sikorski, S. J. Petzold, and W. T. Shearer: *J. Clin. Invest.*, 62, 111, 1978) have shown that chronic lymphatic leukemic cells isolated from patients were higher in poly (ADPR) synthesis than normal cells. It has recently been shown that in Ehrlich ascites cells the histone H1 is ADP ribosylated mainly in the C-terminal fragment (H. C. Braeuer, P. Adamietz, U. Nellessen, and H. Hilz: *Eur. J. Biochem.*, 114, 63, 1981). Kidwell (W. R. Kidwell: *J. Biochem.*, 77, 6, 1975) has postulated that poly ADPR formation acts as a trigger for the cell cycle. NAD+ levels are known to be lower in malignant cells than in normal cells (L. S. Jedeiken and S. Weinhouse: *J. Biol. Chem.*, 213, 271, 1955). This may be due to the greater utilization of NAD+ for poly ADPR synthesis in tumor cells.

Novikoff hepatoma cells have been reported to have twice the poly ADPR synthetase of normal liver cells. (L. Burzio and S. S. Koide: *FEBS Letters*, 20, 29, 1972). Poly ADPR synthetase activity has been shown to be 20 times higher in leukemic lymphoblasts as compared to unstimulated normal lymphocytes (A. R. Lehman, S. Kirk-Bell, S. Shall, and W. J. D. Whish: *Exp. Cell Res.*, 83, 63, 1974). Increased cellular proliferation has clearly been demonstrated to correlate with increased activity of poly ADPR synthetase (For a review see H. Hilz and P. Stone: *Rev. Physiol. Biochem. Pharmacol.*, 76, 1, 1976). Formycin B inhibits cellular proliferation in L-5178Y mouse leukemia cells and it has been postulated by Müller that its cytostatic action is due to inhibition of poly ADPR formation (W. E. G. Müller and R. K. Zahn: *Experientia*, 31, 1014, 1975).

Thus we hypothesized that certain novel dinucleotides could be prepared which might act as substrate analogs that might bind to poly ADPR synthetase but could not be utilized by this enzyme, thus resulting in an inhibition of ADP-ribosylation and in controlling rapid cellular proliferation, which would have a direct application in the treatment of cancer.

Similarly, certain viral regulated ADP-ribosylation processes necessary for viral propagation might also be selectively inhibited by the novel dinucleotides which by inhibition of viral replication could be useful in the treatment of various viral infections.

SUMMARY AND DETAILED DESCRIPTION

The concept of the present invention is to replace the nicotinamide moiety of NAD+ with a unique heterocycle, herein designated as R, containing a carboxamide function which carries no charge at the site of $\beta$-ribosyl attachment. It is known that the pyridine carboxamide function is a good leaving group due to the charge at the pyridine nitrogen. Thus a nucleophilic protein function may become ADP-ribosylated by ADP-ribosyl synthetase due to a Walden inversion at $C_1$ via displacement of the nicotinamide group. To inhibit this process one can remove the charge of the heterocycle at $C_1$ by:

(1) Attachment of the heterocyclic carboxamide R, via an uncharged nitrogen by utilizing a 5-membered ring such as the 1,2,4-triazole-3-carboxamide, or (2) Attachment of R through a carbon-carbon bond such as in the 1,3-thiazole-4-carboxamide or the 1,3-selenazole-4-carboxamide.

Since the new and novel dinucleotides, designated hereinafter as Structure I, carry no formal charge in the heterocycle containing the carboxamide function, these hitherto unknown dinucleotides should be able to penetrate cellular membranes more readily than NAD+ and as ADP-ribosylation inhibitors could have direct application to the chemotherapy of cancer and the treatment of viral infections. It is important that the dinucleotides not inhibit the biochemical oxidation-reduction reactions of NAD+ and its reduced form abbreviated as NADH since this would result in high host toxicity. Thus, the novel dinucleotide cannot readily accept a hydride ion on the atom adjacent to the carboxamide function as in NAD+. Therefore, these novel dinucleotides specifically provided herein are selected such that they do not interfere with the oxidation-reduction metabolic pathways of NAD+-NADH.

The present invention thus relates to a class of novel dinucleotide compounds and methods for their production, which compounds are azolecarboxamide compounds of adenosine diphosphoribose (ADP-R) of the structure I wherein R is a heterocycle selected from 4-carbamoyl-1,3-thiazol-2-yl (a), 4-carbamoyl-1,3-selenazol-2-yl (b), and 3-carbamoyl-1,2,4-triazol-1-yl (c); and physiologically acceptable salts of the azolecarboxamide compounds (I):

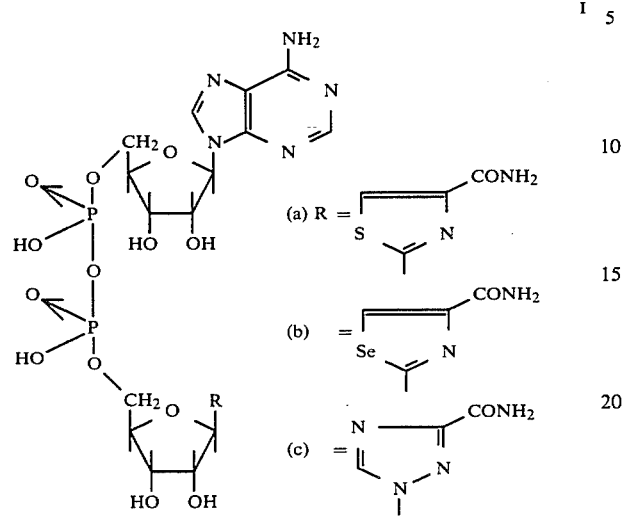

Preferred compounds for the purposes of the invention are the following:

P¹-(Adenosine-5'), P²[(2-β-D-ribofuranosyl-selenazolecarboxamide)-5'-]pyrophosphate (Selenazole-4-carboxamide Adenosine Dinucleotide), P¹-(Adenosine-5'),P²-[(1-β-D-ribofuranosyl-1,2,4-triazole-3-carboxamide)-5'-]pyrophosphate (1,2,4-Triazole-3-carboxamide Adenosine Dinucleoside) and P¹-(Adenosine-5'), P²[(2-β-D-ribofuranosylthiazole-4-carboxamide)-5'-]pyrophosphate (Thiazole-4-carboxamide Adenosine Dinucleotide).

As a general synthetic procedure, nucleotide anhydrides may be prepared by an ion exchange reaction as reviewed by H. G. Khorana ("Some Recent Developments in the Chemistry of Phosphate Esters of Biological Interest," Wiley, New York, 1961), A. M. Michelson ("Synthesis of Nucleotide Anhydrides by Anion Exchange," *Biochim. Biophys. Acta.*, 91, 1–13, 1964), and K. H. Schiet ("Nucleotide Analogs," John Wiley & Sons, New York, 1980). This approach requires that the azolecarboxamide that is to replace nicotinamide in nicotinamide adenosine dinucleotide (NAD+) be converted to its ribotide (phosphoribosylazolecarboxamide) and condensed with adenosine 5'-monophosphate in base such as pyridine. A variety of condensing agents (nonenzymatic catalysts) are available for this synthetic reaction. These mainly serve to activate an oxygen-phosphorus bond such that nucleophilic attack (phosphate-oxygen anion) on the phosphorus atom is facilitated. The condensing agent may be added to a suspension or solution of the requisite azolecarboxamide ribotide and adenosine 5'-monophosphate (A) or the activated nucleotide [either AMP-O-condensing agent (B) or azolecarboxamide-ribose-PO₂-condensing agent (C)] may be preformed and then treated with the other 5'-mononucleotide. In this modification the 5'-mononucleotide may be solubilized and activated for nucleophilic attack by the formation of trialkylammonium or tetraalkylammonium salts (hindered amines):

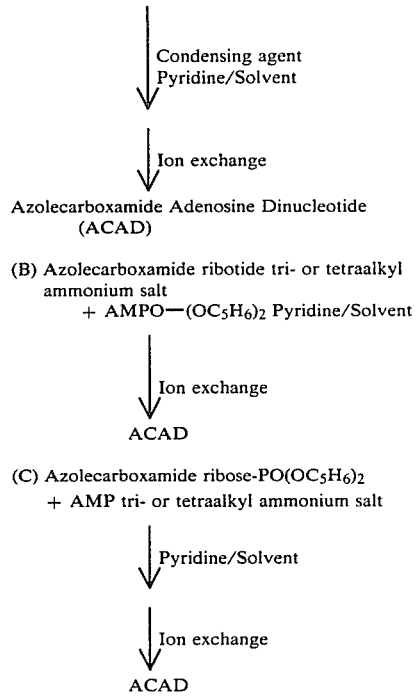

The nucleotide starting materials may be activated according to the invention in any suitable way. For example, the nucleotides may be activated for reaction in situ by condensing agents such as N,N'-dialkylcarbodiimide (DCC) or conversion into isolable, activated phosphates such as triester pyrophosphates [e.g., P'-diphenyl, P²-(adenosine-5'-)pyrophosphates], phosphoramidates (e.g., adenosine 5'-phosphoramidates, -morpholidates, and imidazolidates). The activated phosphate derived from adenosine 5'-monophosphate is the most practical route due to its commercial availability; however, the reverse process (activated phosphate of azolecarboxamide ribotide) is also operational and adds versatility to this process. The azolecarboxamide adenosine dinucleotide final products can be isolated in any suitable way. For example, they conveniently are isolated in pure form by gradient elution from anionic ion exchange chromatography (e.g., AG 1 or 2 and DEAE cellulose).

The compounds of the invention having Structure I are useful antiviral and antitumor agents. Thus, the compounds are typically active, directly or indirectly against viruses such as the DNA vaccinia virus (VV) and the RNA vesicular stomatitis virus (VSV) and leukemias such as L1210 and P388 and solid tumors such as the Lewis lung carcinoma as determined by standard culture assay.

For purposes of providing useful dosage forms, the dinucleotides I singly or in combination are appropriately mixed with a suitable pharmaceutical carrier which may be sterilized water or physiological saline, i.e., pH and salt adjusted solutions suitable for topical, intravenous, intramuscular, or other routes of administration.

Preferredly, the dinucleotides I of the invention are constituted as a solute in an appropriate pharmaceutical carrier. Alternatively, however, suspensions, emulsions, and other formulations of the compounds of the invention could be used where indicated. The pharmaceutical carrier, in addition to having a solubilizing or suspending agent therein, might also include suitable dilultants, buffers, surface active agents, and other similar agents as are typically used in pharmaceutical carriers. The total composition of the pharmaceutical carrier, however, is chosen to be compatible with the site of delivery and with the concentration of the active ingredient.

Each compound of the invention is suitably constituted with the pharmaceutical carrier in a concentration of at least 0.1 percent by weight of the total composition. Preferredly, it would be present in the pharmaceutical carrier at a concentration of about 10% to about 90% by weight of the total composition.

Effective amounts of the dinucleotide, or other compounds of the invention, typically would range from about 2.5 milligrams per kilogram (mg/kg) of the total body weight of the treated warm blooded animal to about 200 mg/kg per day. Preferredly, the range would be from 12.5 mg/kg to about 100 mg/kg. An even more preferred range would be from about 15 mg/kg to about 50 mg/kg. As with other factors noted above, the amount of compound utilized in treating an afflicted animal would take into account parameters such as the type of virus or tumor, the virus or tumor site, the form of administering the compound, and the physical size and condition of the host. In any event, the actual amount should be sufficient to provide a chemotherapeutically effective amount of the agent to the host in a convenient volume.

A composition used for inhibiting malignant tumors in warm blooded animals might be suitably prepared by constituting the dinucleotides of the invention in a pharmacologically compatible solvent followed by sterilization and packaging in appropriate sealable vials at a known concentration. Appropriate doses of the compound are then withdrawn from the vial and administered by injection to the host.

The invention is illustrated by the following examples.

EXAMPLE 1

$P^1$-(Adenosine-5'), $P^2$[(1-$\beta$-D-ribofuranosyl)-1,2,4-triazole-3-carboxamide)-5'-]pyrophosphate (1,2,4-Triazole-3-carboxamide Adenosine Dinucleotide)

To a solution of adenosine 5'-monophosphate (free acid from Sigma Chemical Company, 2.0 g, 5.8 mmol) and 1-$\beta$-D-ribofuranosyl-1,2,4-triazole-3-carboxamide 5'-phosphate (U.S. Pat. No. 3,651,045, 0.97 g, 3 mmol) in water (50 ml, initial warming and stirring is necessary to obtain a clear solution) were added anhydrous pyridine (325 ml) and N,N$^1$-dicyclohexylcarbodiimide (18 ml). The reaction mixture was stirred at 0° C. for 24 hours, and then filtered to remove the precipitated dicyclohexylurea. To the filtrate was added a second portion of DCC (18 ml) and stirring at 0° C. for 24 hours was continued. Precipitated dicyclohexylurea was filtered. This process was repeated three more times so that a total of 90 ml of DCC were used. Finally, the filtrate was poured into water (2 l) and stirred at room temperature for two hours. The solution was filtered, and the filtrate was washed with chloroform (3×350 ml) and the aqueous solution was concentrated under reduced pressure to about 50 ml. The pH of the solution was adjusted to six and applied to a column (20 cm×6 cm) of Dowex-2 resin (formate form). The column was washed with water (4 l) to remove inorganic salts, followed by a gradient elution (water to 0.2 N formic acid, 1 l each).

The novel dinucleotide was eluted first, followed by adenosine 5'-monophosphate and then $P^1P^2$-diadenosine 5'-pyrophosphate. The homogeneous fractions containing the novel nucleotide were combined and concentrated under reduced pressure (<30° C.) to about 100 ml, frozen, and lyophilized to provide the title product as a white amorphous solid (0.8 g); UV λ max (pH 1) 256 nm (ε 23,800), λ max (pH 7) 258 (25,100), λ max (pH 11) 258 (25,800); 1$_H$NMR (Me$_2$SO-d$_6$)δ 8.50 (s, 1, C$_5$H from trizole), 8.30 and 8.20 (s, 1, C$_2$$\underline{H}$ and C$_8$$\underline{H}$ from AMP), 7.73 (bs, 4, NH$_2$ and CON$\underline{H_2}$, exchanges with D$_2$O), 6.0 (d, J=5 Hz) and other sugar protons.

EXAMPLE 2

$P^1$-(Adenosine-5'-), $P^2$-[(2-$\beta$-D-ribofuranosylthiazole-4-carboxamide)-5'-]pyrophosphate (Thiazole-4-carboxamide Adenosine Dinucleotide).

2-$\beta$-D-Ribofuranosylthiazole-4-carboxamide. Ethyl 2-(2,3,5-tri-O-benzoyl-$\beta$-D-ribofuranosyl)-thiazole-4-carboxamide was utilized as prepared in Srivastava et al., *J. Med. Chem.*, 1977, 20, No. 2, 256, herein incorporated by reference. A concentrated solution of ethyl 2-(2,3,5-tri-O-benzoyl-$\beta$-D-ribofuranosyl)thiazole-4-carboxamide (5.0 g, 8.31 mmol) in methanol (15 ml) was stirred with methanolic ammonia (saturated at 0° C., 100 ml) in a pressure bottle at room temperature for two days. The solvent was evaporated and the residue was chromatographed through a column (2.5×35 cm) of silica gel (100 g) packed in ethyl acetate. Elution of the column with a solvent system (ethyl acetate-1-propanol-water, 4:1:2; v/v; top layer) removed the fast-moving methyl benzoate and benzamide. The slower moving, major, UV and sugar-positive fractions were collected and the solvent was evaporated in vacuo. The residue (syrup), thus obtained, was readily crystallized from ethanol-ethyl acetate to provide 1.6 g (74%) of pure product; mp 144°–145° C.; [α]$_D^{25}$ 14.3° (c 1, DMF); UV λ max (pH 1) 237 nm (8640); UVλ max (pH 11) 238 (8100); $^1$H NMR (Me$_2$SO-d$_6$)δ 7.5 7.8 (bs, 2, CONH$_2$)δ4.99 (d, 1, J=5 Hz, H$_1$'), 8.25 (s, 1, H$_5$).

2-(5-O-Phosphono-$\beta$-D-ribofuranosyl)thiazole-4-carboxamide (2-$\beta$-D-Ribofuranosylthiazole-4-Carboxamide 5'-Phosphate). Water (151 mg, 8.4 mmol) was added carefully to a solution (maintained at 0° C. with stirring) of freshly distilled phosphoryl chloride (2.0 g, 13.2 mmol), pyridine (1.21 g, 14.4 mmol) and acetonitrile (2.3 g, 56.7 mmol). 2-$\beta$-D-Ribofuranosylthiazole-4-carboxamide (powdered and dried over P$_2$O$_5$, 800 mg, 3.0 mmol) was added to the solution and the reaction mixture was stirred continuously for four hours at 0° C. The reaction mixture was poured into ice water (ca. 50 ml) and the pH was adjusted to 2.0 with 2 N sodium hydroxide. The solution was applied to a column of activated charcoal (20 g), and the column was washed thoroughly with water until the eluate was salt-free. The column was eluted with a solution ethanol-water-concentrated ammonium hydroxide (10:10:1) and 25 ml fractions were collected. The fractions containing pure (tlc, silica gel, acetonitrile-0.1 N ammonium chloride (7:3)) nucleotide were collected and evaporated to dryness under vacuum. The anhydrous residue was dissolved in water and passed through a column of Dowex 50 W-X8 (20–50 mesh, H$^+$ form, 15 ml). The column was washed with water and the fraction containing the nucleotide was collected. The solution was concentrated to a small volume (5 ml), adjusted to pH 8 with 1 N sodium hydroxide solution and placed on a column of Bio-Rad AG 1×8 (formate form, 50–100 mesh, 20 ml). The column was first washed with water (100 ml) and then with a gradient of 0.2 M to 0.5 M formic acid (300 ml each).

The product appeared after ca. 375 ml of gradient had passed through the column. The pure fractions were pooled and evaporated under reduced pressure (<30° C.) to a small volume. Addition of ethanol (35 ml) provided the desired nucleotide as the free acid as a white powder (ca. 500 mg) after washing successively with ethanol and ether and drying at 50° for five hours.

$P^1$-(Adenosine-5'-)$P^2$-[(2-β-D-ribofuranosylthiazole-4-carboxamide)-5'-]pyrophosphate (Thiazole-4-carboxamide Adenosine Dinucleotide). The title dinucleotide is prepared by condensing 2-β-D-ribofuranosylthiazole-4-carboxamide 5'-phosphate (free acid, 1.02 g, 3 mmol) with adenosine 5'-phosphate (Sigma Chemical Company, 2.0 g, 5.8 mmol) in pyridine-water at 0° C. as described in EXAMPLE 1. The crude material was isolated and purified by ion exchange chromatography (Dowex-2, formate form) as described in EXAMPLE 1. The novel thiazolecarboximide adenosine dinucleotide was obtained as a white powder (800 mg); UV λ max (pH 1) 256 nm (ε 10,600), λ max (pH 7) 257 (11,800), λ max pH 11) 257 (12,200):$^1$H' NMR (Me$_2$SO-d$_6$) δ 6.0 (d, 1, J=5 Hz, H$_1$'), 8.3 (s, 1, C$_5$H), 8.5 (s, 1, C$_8$H), 8.7 (s, 1, C$_2$H); ir (KBr) 1680 cm$^{-1}$ (C=O).

EXAMPLE 3

$P^1$-(Adenosine-5'-), $P^2$-[(2-β-D-ribofuranosyl-selenazole-4-carboxamide)-5'-]pyrophosphate (Selenazole-4-carboxamide Adenosine Dinucleotide).

Reaction of 2,5-Anhydro-3,4,6-Tri-O-Benzoyl-D-Allonselenocarboxamide with Ethyl Bromopyruvate and the Synthesis of Ethyl 2-(2,3,5-Tri-O-Benzoyl-D-Ribofuranosyl)selenazole-4-Carboxylates. A solution of 2,5-anhydro-3,4,6-tri-O-benzoyl-D-allonselenocarboxamide (5.5 g, 10 mmol) in acetonitrile (60 ml) was cooled in ice. Ethylbromopyruvate (3.0 g) in acetonitrile (20 ml) was added dropwise (ten minutes). The ice bath was removed and the reaction mixture was stirred at room temperature for one hour. The solvent was evaporated in vacuo and the residue was triturated with a saturated sodium bicarbonate solution (100 ml) and extracted with ethyl ether (2×100 ml). The combined ether portion was washed with water and dried (MgSO$_4$). The ether was evaporated in vacuo and the residue (syrup) was passed through a silica gel (300 g) column packed in chloroform. Elution with 5% ethylacetate in chloroform provided subtitle products: namely the fast moving ethyl 2-(2,3,5-tri-O-benzoyl-2-β-D-ribofuranosyl)-selenazole-4-carboxylate (2.5 g) and the slow moving ethyl 2-(2,3,5-tri-O-benzoyl-2-α-D-ribofuranosyl)-selenazole-4-carboxylate (1.0 g).

2,5-Anhydro-3,4,6-Tri-O-Benzoyl-D-Allonselenocarboxamide. A mixture of 2,3,5-tri-O-benzoyl-β-D-ribofuranosylcyanide (10.0 g, 21.2 mmol), 4-dimethylaminopyridine (200 mg) and liquid hydrogenselenide (200 mg) and liquid hydrogenselenide condensed under N$_2$ atmosphere, 20 ml) was stirred in a sealed bomb at room temperature for 20 hours. Hydrogen selenide was allowed to evaporate. The dark colored residue was dissolved in chloroform (200 ml) and washed successively with water (3×50 ml), saturated NaHCO$_3$ (3×50 ml) followed by water (2×50 ml). The chloroform portion was dried (MgSO$_4$) and evaporated under vacuum to provide the subtitle product as a foam in almost quantitative yield. The latter product of analytical purity was provided by column chromatography (silica gel, 5% ethyl acetate in chloroform). The product developed a purple color when the silica gel chromatogram of the product was sprayed with a dilute ethanolic solution of 2,3-dichloronaphthopurinone and exposed to ammonia.

Analysis calculated for C$_{27}$H$_{23}$NO$_7$Se: C, 58.91; H, 4.21; N, 2.54; Se, 13.98. Found: C, 58.81; H, 4.29; N, 2.51; Se, 13.74.

2-β-D-Ribofuranosylselenazole-4-carboxamide. Ethyl 2-(2-3,5-tri-O-benzoyl-β-D-ribofuranosyl) selenazole-4-carboxylate (3.2 g, 5 mmol) was dissolved in methanol (100 ml), cooled and saturated with ammonia (0° C.). The solution was stirred in a pressure bottle at room temperature for 48 hours. The solvent was evaporated in vacuo and the residue was extracted with chloroform (25 ml×3). The chloroform portion was discarded. The residue was absorbed on silica gel (10 g) with the aid of methanol and applied on a silica gel column (2.8×45 cm) packed in ethyl acetate. The column was eluted with solvent E (ethyl acetate, n-propanol, H$_2$O; 4:1:2; v/v; top layer provides solvent E) and the homogeneous fractions (Rf≈0.42, silica gel tlc in solvent E) containing the major product were collected. The solvent was evaporated in vacuo and the title product as a residue was crystallized from 2-propanol: yield 900 mg of the title product (60%) mp 135°–136° C. The residue provided a second crop (200 mg) with mp 131°–133° C.

Analysis calculated for C$_9$H$_{12}$N$_2$O$_5$Se: C, 35.19; H, 3.94; N, 9.12: Se, 25.71. Found C, 35.43; H, 3.97; N, 9.03; Se, 25.55.

2-β-D-Ribofuranosylselenazole-4-carboxamide 5'-phosphate. Water (151 mg, 8.4 mmol) was added carefully to a solution (maintained at 0° C. by stirring) of phosphoryl chloride (2.0 g, 13.2 mmol), pyridine (1.21 g, 14.4 mmol) and acetonitrile (2.3 g, 56.7 mmol). 2-β-D-Ribofuranosylselenazole-4-carboxamide (921 mg, 3.0 mmol) was added to the solution and the mixture was stirred for four hours at 0° C. A clear solution was obtained which was poured into ice water (50 ml) and the pH was adjusted to 2.0 with concentrated sodium hydroxide. The solution was applied to a column of activated charcoal (30 g), and the column was washed thoroughly with water until the eluate was salt free. The column was eluted with a solution of ethanol-water-concentrated ammonium hydroxide (10:10:1) and the fractions (25 ml each) were collected. The fractions containing the nucleotide product, (tlc, silica gel, acetonitrile - 0.1 N ammonium chloride (7:3)) were collected and evaporated to dryness under vacuum. The anhydrous residual product was dissolved in water and passed through a column of Dowex 50W-X8 (20–50 mesh, H$^+$ form, 15 ml). The column was washed with water and the fraction containing the nucleotide was collected. The solution was concentrated to a small volume (5 ml), adjusted to pH 8 with 1 N sodium hydroxide solution, and placed on a column of Bio-Rad AG 1×8 (formate form, 50–100 mesh, 20 ml). The column was first washed with water (100 ml) and then with a gradient of 0.2 M to 0.5 M formic acid (300 ml each). The product appeared after ca. 375 ml of gradient had passed through the column. The pure fractions were pooled and evaporated under reduced pressure (<30° C.) to a small volume. Addition of ethanol (35 ml) provided the desired nucleotide as the free acid as a white powder (ca. 500 mg) after washing successively with ethanol and ether and drying at 50° for five hours.

$P^1$-(Adenosine-5'-), $P^2$-[(2-$\beta$-D-ribofuranosyl-selenazole-4-carboxamide)-5'-]pyrophosphate (Selenazole-4-carboxamide Adenosine Dinucleotide). 2-$\beta$-D-Ribofuranosylselenazole-4-carboxamide-5' phosphate (free acid, 3.41 g, 10 mmol) is suspended in methanol (70 ml) and tri-n-octylamine (3.39 g, 10 mmol) added. The suspension is then refluxed until a clear solution is obtained (ca. five minutes). Solvent is removed under reduced pressure and traces of moisture removed from the residue by dissolution in dimethyl formamide followed by evaporation to dryness under reduced pressure. The residue is dissolved in dioxan (70 ml) and treated with a solution of $P^1$-adenosine-5¹, $P^2$-diphenyl pyrophosphate (5.81 g, 10 mmol) in dioxan (10 ml) and pyridine (23 ml) prepared as described below. To a solution of the tri-n-octylammonium salt (prepared as above) of adenosine 5'-monophosphate (6.98 g, 10 mmol) in dioxane (70 ml) is added diphenyl phosphochloridate (3 ml) and tri-n-butylamine (4.5 ml) and the clear solution kept at room temperature for two hours under anhydrous conditions. Solvent is then removed under reduced pressure, and ether added to the residue with shaking to precipitate $P^1$-adenosine-5', $P^2$-diphenyl pyrophosphate. The mixture is kept at 0° C. for 30-60 minutes and then ether is removed by decantation. Dioxan (20 ml) is added to the precipitated material and the solution concentrated to a syrup under reduced pressure to remove ether and traces of moisture. The residue was dissolved in dioxan and pyridine and vigorously stirred with the tri-n-octylamine salt of 2-$\beta$-D-ribofuranosylselenazole-4-carboxamide 5'-phosphate (prepared above) at room temperature for three hours. The solution was mixed with dry ether (600 ml), and the precipitated crude dinucleotide collected by centrifugation, washed twice with ether, and dried. The crude salt was dissolved in water and adjusted to pH 6 with 1 N sodium hydroxide and applied to a column of AG 1×8 ion exchange resin (60×6 cm, formate form). The column was washed with water (3 l) to remove inorganic salts followed by gradient elution (water to 0.2 N formic acid, 1 l each). The fractions containing the pure selenazolecarboxamide adenosine dinucleotide were pooled and evaporated under reduced pressure (<30° C.) to a small volume. Addition of ethanol (100 ml) precipitated the dinucleotide. This was filtered, washed with ethanol and then ether, and dried at 40°, 0.5 torr for 24 hours to afford the title selenazole-4-carboxamide adenosine dinucleotide as a white powder (2.0 g); UV $\lambda$ max (pH 1) 255 nm ($\epsilon$ 10,700), $\lambda$ max (pH 7) 256 (12,000), $\lambda$ max (pH 11) 256 (12,400); ir (KBr) 1680 cm$^{-1}$ (CONH$_2$).

EXAMPLE 4

The dinucleotides of Structure I may be prepared either by procedure A (above), that is by condensation of the appropriate azolecarboxamide 5'-ribotide with adenosine 5'-phosphate in the presence of dicyclohexylcarbodiimide in pyridine-water as described in EXAMPLE 1 or by procedure B (above), which is the reaction of preformed azolecarboxamide 5'-ribotide tri- or tetraalkylammonium salts with preformed $P^1$-adenosine, $P^2$-diphenylpyrophosphate in dioxan-pyridine as described in EXAMPLE 3.

EXAMPLE 5

The dinucleotide free acids as isolated in EXAMPLES 1-3 are each converted into amine or alkaline metal salts by passage of an aqueous solution of the respective dinucleotide free acid through ion exchange resin (Dowex 50W×8) prepared in the desired counter ion (e.g. Na+ Li+, K+, pyridine, tri-N-butylamine, etc). Thus, using sodium ion exchange resin the following sodium salts of the invention are obtained: $P^1$(adenosine-5'-),$P^2$-[(1-B-D-ribofuranosyl-1,2,4-triazole-3-carboxamide)-5'-]pyrophosphate, sodium salt; $P^1$(adenosine-5'-),$P^2$-[(2-$\beta$-D-ribofuranosylthiazole-4-carboxamide)-5'-]pyrophosphate, sodium salt; and $P^1$-(adenosine-5'), $P^2$-[(2-$\beta$-D-ribofuranosylselenazole-4-carboxamide)-5'-]pyrophosphate, sodium salt.

EXAMPLE 6

Antiviral Evaluation. Inhibition of the virus-induced cytopathic effect (CPE) was used as the indicator of azolecarboxamide adenosine dinucleotide antiviral activity. Inhibition of CPE was observed in African green monkey kidney (Vero, V) cells after infection with herpes simplex virus, type 1 (HSV/1); vaccinia virus (VV); parainfluenza virus, type 3 (PIV/3), and vesicular stomatitis virus (VSV). In these experiments, monolayers (18 h) of cells were exposed to 320 TCID$_{50}$ of virus and concentrations of each compound ranging in one-half log dilutions from 1,000 to 1 $\mu$g/ml were added within 15 to 30 minutes. The degree of CPE inhibition and compound cytotoxicity were observed microscopically after 72 hours of incubation at 37° C. and scored numerically in order to calculate a virus rating (VR) as previously described by Sidwell, et. al., *Appl. Microbiol.*, 22, 97 (1971). Significance of antiviral activity in terms of VRs has been assigned as follows: <0.5, slight or no activity, 0.5-0.9, moderate activity, and $\geq$1.0, marked activity. The virus rating (VR) of the dinucleotides having Structure I range from 0.7 to 1.2. For example, dinucleotide Ic exhibits a VR of 1.2 against the DNA virus vaccinia (VV) and a VR of 0.7 against the RNA virus vesicular stomatitis (VSV).

EXAMPLE 7

Antitumor Evaluation. L1210 cells, a murine leukemia cell line, were grown in RPMI 1640 supplemented with 5% fetal bovine serum and gentamicin (50 $\mu$g/ml).

Drug dilutions were prepared in the appropriate solvent and 20 $\mu$l of each dilution were added to 24-well Linbro tissue culture plates followed by the addition of 2.0 ml of cell suspension containing 3×10⁴ cells per ml. Solvent and medium controls were included in each test. After incubation at 37° C. for three days in 5% CO$_2$, the contents of each well were removed and the cells counted in a ZBI Coulter counter. Percent growth was calculated relative to the controls and the levels of drug activity were expressed as ID$_{50}$ in $\mu$g/ml using probit paper. Using this assay, the dinucleotides of Structure I are active against leukemias L1210 and P388 and the Lewis lung carcinoma. For example, in the L1210 leukemia cell culture system Structure Ia has an ID$_{50}$ of 4.2×10$^{-5}$ and Structure Ic has an ID$_{50}$ of 3.5×10$^{-5}$.

EXAMPLE 8

The purity and mobility of novel dinucleotides of Structure I were examined by high pressure liquid chromatography (HPLC). A Beckman HPLC, model 322, was equipped with a Hidatachi variable wave length spectrophotometer (model C-RIA) with peak integrator, and a reverse phase column (C-18 ODC Beckman 4.6×25 cm). The dinucleotides of Structure I and appropriate comparison samples were dissolved in water and applied to the column by injection. A gradient elution system of 0.1 $KH_2PO_4$ and 5 mM tetrabutylammonium phosphate buffer (pH 5) cleanly separated all peaks. Retention times were for Structure Ia, 13.93 minutes; Structure Ib, 14.05 minutes; adenosine 5'-phosphate, 14.22 minutes; adenosine 5'-diphosphate, 22.68 minutes; and adenosine 5'-triphosphate, 26.08 minutes.

Dinucleotides of Structure I were found by this HPLC instrumentation and developing system to be highly pure. For example, dinucleotide Ia was 98.3% pure and dinucleotide Ib was 97.7% pure.

What is desired to claim as our exclusive privilege and property in the invention as described is the following:

We claim:

1. Azolecarboxamide adenosine dinucleotide compounds having the structural formula:

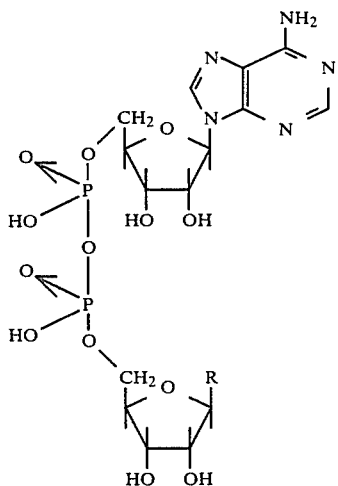

and the pharmaceutically acceptable salts of the compounds; wherein R is a heterocycle that is 3-carbamoyl-1,2,-4-triazol-1-yl or 4-carbamoylselenazol-2-yl.

2. $P^1$-(Adenosine-5'-), $P^2$-[(1-B-D-ribofuranosyl-1,2,4-triazole-3-carboxamide)-5'-]pyrophosphate and pharmaceutically acceptable salts thereof.

3. A compound according to claim 2 which is $P^1$-(adenosine-5'-), $P^2$-[1-B-D-ribofuranosyl-1,3,4-triazole-3-carboxamide)-5'-[pyrophosphate.

4. A compound according to claim 2 which is $P^1$-(adenosine-5'-), $P^2$-[(1-B-D-ribofuranosyl-1,2,4-triazole-3-carboxamide)-5'-[pyrophosphate, sodium salt.

5. A compound according to claim 1 which is $P^1$-(adenosine-5'-),$P^2$-[(2-$\beta$-D-ribofuranosylselenazole-4-carboxamide)-5'-[pyrophosphate and pharmaceutically acceptable salts thereof.

6. A compound according to claim 1 which is $P^1$-(adenosine-5'-),$P^2$-[(2-$\beta$-D-ribofuranosylselenazole-4-carboxamide)-5'-[pyrophosphate.

7. A compound according to claim 1 which is $P^1$-(adenosine-5'-),$P^2$-[(2-$\beta$-D-ribofuranosylselenazole-4-carboxamide)-5'-[pyrophosphate, sodium salt.

* * * * *

UNITED STATES PATENT AND TRADEMARK OFFICE
CERTIFICATE OF CORRECTION

PATENT NO. : 4,544,741

DATED : October 1, 1985

INVENTOR(S) : Roland K. Robins & Ganapathi R. Revankar

It is certified that error appears in the above-identified patent and that said Letters Patent is hereby corrected as shown below:

Column 12, line 24 "1,2,-4-triazol" should be --1,2,4-triazol--.

Column 12, line 30 "-5'-[pyrophosphate." should be -- -5'-]pyrophosphate.--

Column 12, line 33 "5'-[pyrophosphate, sodium salt." should be --5'-]pyrophosphate, sodium salt.--

Column 12, line 37 "5'-[pyrophosphate and pharmaceutially acceptable salts thereof." should be --5'-]pyrophosphate and pharmaceutically acceptable salts thereof.--

Column 12, line 40 "5'-[pyrophosphate." should be --5'-]pyrophosphate.--

Column 12, line 44 "5-[pyrophosphate, sodium salt." should be --5-]pyrophosphate, sodium salt.--

Signed and Sealed this

Twenty-fifth Day of November, 1986

Attest:

DONALD J. QUIGG

Attesting Officer   Commissioner of Patents and Trademarks